United States Patent [19]
Proch et al.

[11] Patent Number: 6,126,592
[45] Date of Patent: Oct. 3, 2000

[54] ENDOSCOPE CLEANING AND IRRIGATION SHEATH

[75] Inventors: Francis S. Proch, Somerville; Patrick Ireland, Memphis, both of Tenn.

[73] Assignee: Smith & Nephew, Inc., Memphis, Tenn.

[21] Appl. No.: 09/152,128

[22] Filed: Sep. 12, 1998

[51] Int. Cl.$^7$ ................................................. A61B 1/012
[52] U.S. Cl. .......................... 600/114; 600/157; 600/158; 600/156; 600/129
[58] Field of Search ..................... 600/156, 157, 600/158, 153, 171, 114, 128, 129

[56] References Cited

U.S. PATENT DOCUMENTS

| | | | |
|---|---|---|---|
| 3,850,162 | 11/1974 | Iglesias | 600/156 |
| 3,850,175 | 11/1974 | Iglesias | 600/156 |
| 3,903,877 | 9/1975 | Terada . | |
| 4,281,646 | 8/1981 | Kinoshita . | |
| 4,497,550 | 2/1985 | Ouchi et al. . | |
| 4,509,507 | 4/1985 | Yabe . | |
| 4,548,197 | 10/1985 | Kinoshita . | |
| 4,576,146 | 3/1986 | Kawazoe et al. . | |
| 4,667,655 | 5/1987 | Ogiu et al. . | |
| 4,779,624 | 10/1988 | Yokoi . | |
| 4,815,450 | 3/1989 | Patel . | |
| 4,844,052 | 7/1989 | Iwakoshi et al. . | |
| 4,878,485 | 11/1989 | Adair . | |
| 4,991,565 | 2/1991 | Takahashi et al. . | |
| 5,037,386 | 8/1991 | Marcus et al. | 600/156 |
| 5,170,774 | 12/1992 | Heckele | 600/156 |
| 5,207,213 | 5/1993 | Auhll et al. . | |
| 5,237,984 | 8/1993 | Williams, III et al. . | |
| 5,313,934 | 5/1994 | Wiita et al. . | |
| 5,386,817 | 2/1995 | Jones | 600/157 |
| 5,464,008 | 11/1995 | Kim | 600/157 |
| 5,486,154 | 1/1996 | Kelleher . | |
| 5,509,892 | 4/1996 | Bonnet . | |
| 5,518,502 | 5/1996 | Kaplan et al. . | |
| 5,533,496 | 7/1996 | De Faria-Correa et al. | 600/157 |
| 5,536,234 | 7/1996 | Newman | 600/156 |
| 5,575,756 | 11/1996 | Karasawa et al. . | |
| 5,630,795 | 5/1997 | Kuramoto et al. . | |
| 5,647,840 | 7/1997 | D'Amelio et al. . | |
| 5,697,888 | 12/1997 | Kobayashi et al. | 600/157 |

FOREIGN PATENT DOCUMENTS

| | | |
|---|---|---|
| 0791336 | 8/1997 | European Pat. Off. . |
| 9428782 | 12/1994 | WIPO . |
| 9502988 | 2/1995 | WIPO . |

*Primary Examiner*—John P. Leubecker
*Attorney, Agent, or Firm*—Fulbright & Jaworski L.L.P.

[57] ABSTRACT

An improved disposable sheath for a medical endoscope of the type that includes an elongated bundle of optical fibers for viewing an internal surgical site, the endoscope including a distal tip adapted to transmit images from the surgical site through the fibers. The improved sheath having an elongated housing with proximal and distal ends in which the distal end has top and bottom portions. A first opening extends through the housing for receiving the endoscope and a second opening extends though the housing for transmitting fluid through the housing. The proximal end of the housing is adapted to secure the housing relative to the endoscope and to connect the second opening to a source of fluid. The first opening is unobstructed at the distal end of the housing to allow the distal tip of the endoscope to project past the top portion of the distal end. The bottom portion of the housing distal end extends beyond the distal tip of the endoscope. The second opening of the housing extends through the bottom portion of the housing distal end so that fluid flowing out of the second opening will clean the distal tip of the endoscope.

12 Claims, 3 Drawing Sheets

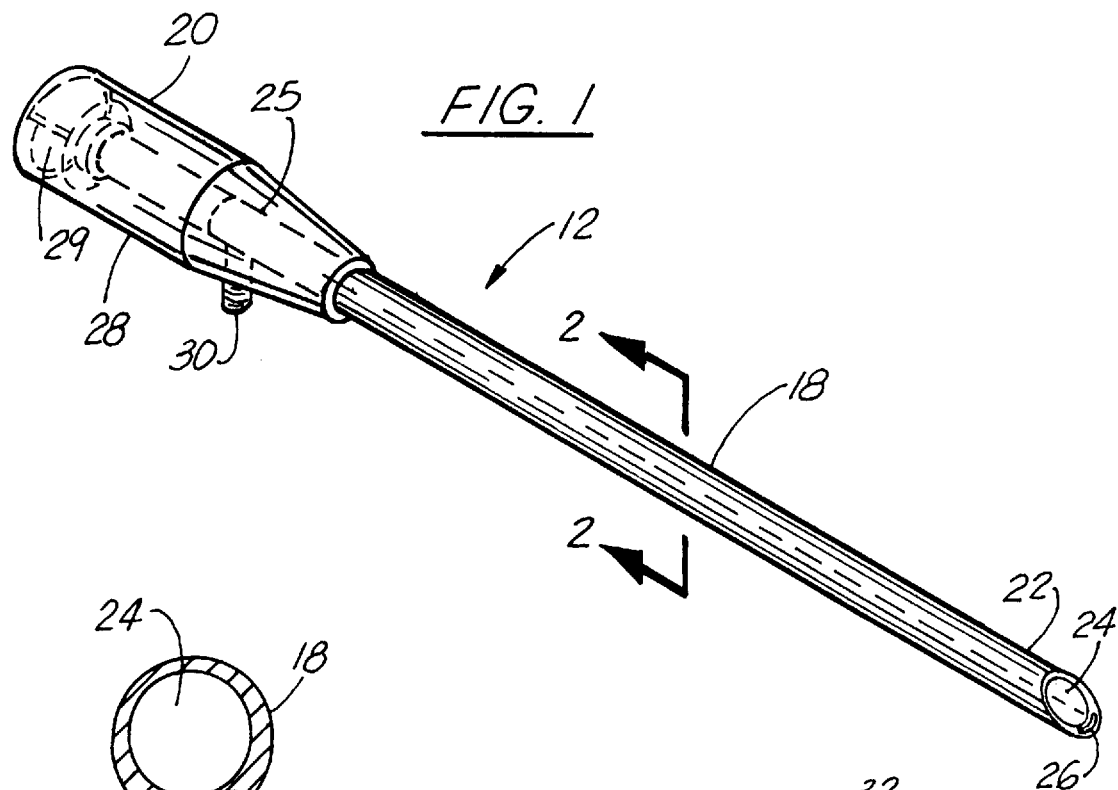
FIG. 1
FIG. 2
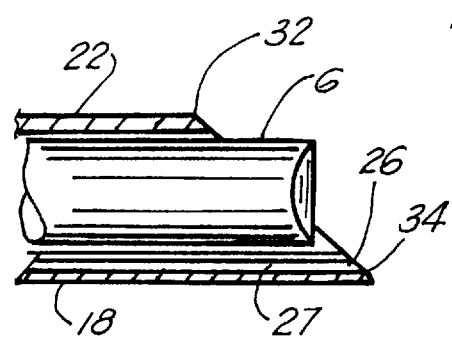
FIG. 3
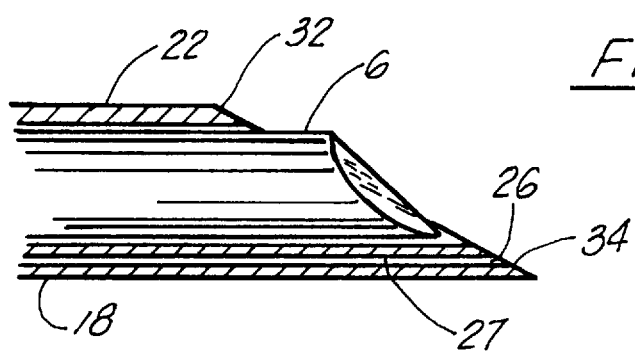
FIG. 4

ENDOSCOPE CLEANING AND IRRIGATION SHEATH

FIELD OF THE INVENTION

This invention relates to disposable sheaths for medical endoscopes and more particularly to disposable sheaths that are effective in cleaning the viewing end of such an endoscope when it is in the surgical field and a system and method for cleaning the viewing end of such an endoscope.

BACKGROUND OF THE INVENTION

A bundle of optical fibers in present day endoscopes permit remote visual examination of a surgical site while a surgical procedure is being performed. During surgery, blood, tissue or other bodily material from the surgical site can splatter onto the viewing end of the endoscope and obscure the field of view through the endoscope. In some instances, it is necessary to remove the endoscope from the surgical site to clean its viewing end. This process usually interrupts and undesirably prolongs the surgical procedure. Because of the inconvenience of removing and cleaning an endoscope during surgery, some surgeons prefer to use a sheath over the endoscope that allows for flushing away any surgical debris that obscures the view through the endoscope.

Known endoscope sheaths, such as shown in U.S. Pat. Nos. 4,991,565 and 4,974,480, are usually custom fitted to the endoscope. The sheath can include tubes for air, water and suction to flush away or suction out surgical debris from the viewing end of the endoscope. The irrigation, suction and air tubes on the endoscope sheath add significant width to the profile of the endoscope and, therefore, require an incision of corresponding size to accommodate the endoscope and sheath.

Disposable sheaths for medical endoscopes that have a low profile and are designed to flush debris from the viewing end of the endoscope are described in PCT published applications WO 95/02988 and WO 94/28782. Endoscope sheaths are used to clean the tip of endoscopes such as the Endoscrub sold by Xomed. However, these devices are not satisfactory because they have a tendency to leave water on the viewing end of the endoscope which can obstruct the surgeon's vision. Other devices that attempted to solve this problem include a product known as the Richard Wolf Suction/Irrigation Sheath which is large and unwieldy.

It would be desirable to provide and endoscope sheath cleaning system that allows for the cleaning of the end of an endoscope during surgery by supplying a controlled amount of irrigation fluid to the end of the lens and to then remove the fluid. It would also be desirable to provide an endoscopic sheath cleaning system that supplies a controllable irrigation stream for irrigating the surgical field.

SUMMARY OF THE INVENTION

The problems discussed above have been solved by the disposable sheath cleaning and irrigation system of the present invention and its method of use. The improved disposable sheath is an elongated housing with proximal and distal ends and a first opening extending through the housing for receiving the endoscope. A second opening extends though the housing, parallel to the first opening, for transmitting fluid through the housing. The proximal end of the housing is adapted to secure the housing relative to the endoscope and to connect the second opening to a source of fluid. The first opening is unobstructed at the distal end of the housing in order to allow the distal tip of the endoscope to project past a top portion of the distal end. A bottom portion of the distal end extends beyond the distal tip of the endoscope. The second opening extends through the bottom portion of the distal end of the housing so that fluid flowing out of the second opening will clean the distal tip of the endoscope.

The invention also includes a cleaning and stream irrigating system, which includes a source of cleaning and irrigating fluid. A reversible pump is connected to the source of fluid and a conduit in the housing for selectively irrigating and evacuating fluid from the surgical site. A fluid control mechanism includes a first and second foot pedal, connected to the pump for allowing the surgeon to control the direction and amount of fluid flow through the conduit of the housing. The first foot pedal is changeable from first to second positions when the pedal is depressed, with the pedal automatically being spring biased toward the first position when the pedal is not depressed. The second foot pedal, which when depressed, signals the pump to supply fluid to the conduit at a plurality of predetermined rates. When the second pedal is allowed to return to its first position, the pump automatically reverses the flow of fluid for a relatively short period of time at a predetermined rate to evacuate fluid from the distal end of the endoscope.

The invention also includes a method for cleaning and stream irrigating the viewing end of a medical endoscope.

BRIEF DESCRIPTION OF THE DRAWINGS

The invention will become more apparent when the detailed description of the exemplary embodiments is considered in conjunction with the appended drawings, in which:

FIG. 1 is a perspective view of the disposable sheath of the subject invention with certain structures in phatom;

FIG. 2 is a cross-sectional view of the sheath on FIG. 1 along lines 2—2;

FIG. 3 is a side partial cross-sectional view of a portion of the distal end of the sheath of FIG. 1;

FIG. 4 is a side partial cross-sectional view of a portion of an alternate embodiment of the distal end of the sheath of FIG. 1;

DETAILED DESCRIPTION OF THE PREFERRED EMBODIMENT

Figure 6:
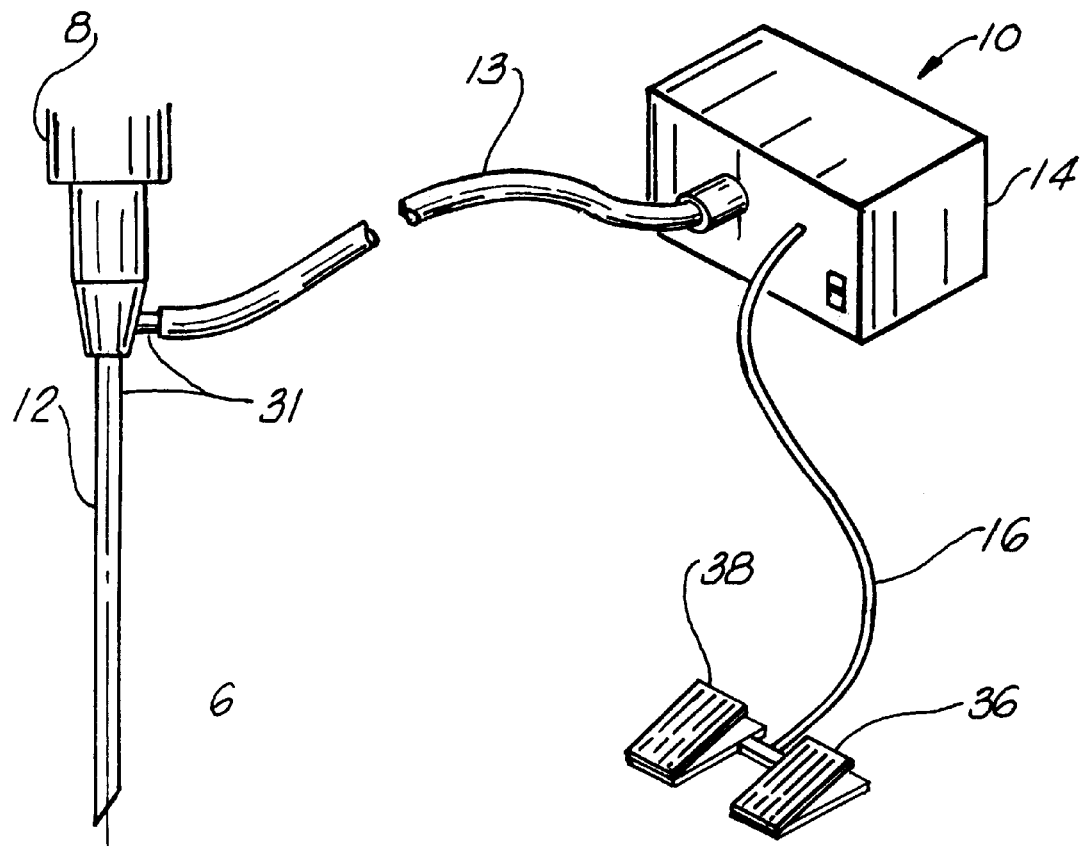
FIG. 6 is a schematic view of the cleaning/stream irrigation system of the subject invention.

An endoscopic cleaning/stream irrigation system 10 of the present invention includes a disposable sheath 12, a source of fluid 13 connected to a reversible pump 14 and a control 16 for the pump 14, as illustrated in FIG. 6. The cleaning/ stream irrigation system 10 of the present invention is used for cleaning the viewing or distal end 6 of an endoscope 8 and for irrigating the surgical field. The disposable sheath 12 includes an elongated housing 18 having proximal and distal ends 20, 22 (FIG. 1). A first opening 24 extends longitudinally through the housing 18 for receiving the endoscope 8 and a second opening 26 extending longitudinally through a portion of the housing 18 for transmitting fluids through the housing 18. The first and second openings 24, 26 are in parallel alignment with each other. The second opening 26 has a proximal and distal end 25, 27. In a preferred embodiment, the first opening 24 is generally circular in cross section and the second opening 26 is generally are-shaped (FIG. 2). The housing 18 is preferably formed of a single piece of sterilizable polymer.

The proximal end 20 of the housing 18 includes a hub portion 28 that in a preferred embodiment has a generally larger circumference than the circumference of the housing 18. The hub portion 28 includes a locking mechanism 29 that will engage a portion of the endoscope 8 in order to lock it within the first opening 24 of the elongated housing 18 (FIG. 1). In a preferred embodiment, the hub portion 28 is configured to provide a handgrip for the user. The hub portion 28 also includes a nipple 30 preferably placed perpendicular to and intersecting the second opening 26 of the housing 18 for a connection to a source of fluid 13. As shown in FIG. 1, the proximal end 25 of the second opening 26 terminates a short distance past the intersection of the nipple 30 so as to allow the flow of fluid through the nipple 30 and the second opening 26 and out the distal end 27 of the second opening 26. Thus, the second opening 26 and the nipple 30 provide a conduit 31 in the housing 18 for selectively irrigating and evacuating fluid from the surgical site.

Figure 5:
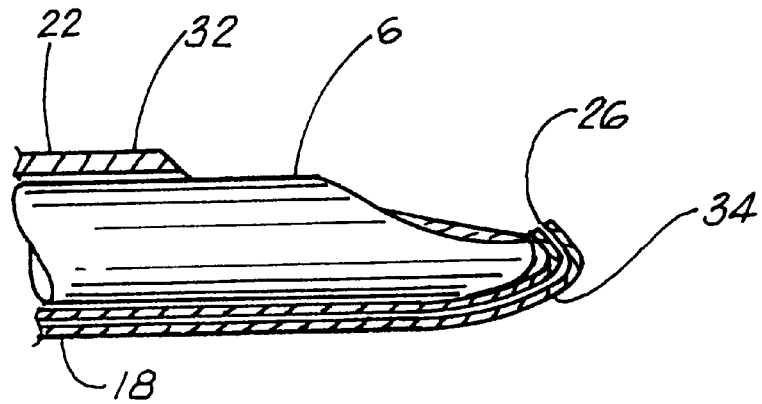
FIG. 5 is a side partial cross-sectional view of a portion of another alternate embodiment of the distal end of the sheath of FIG. 1.

In a preferred embodiment, the distal end 22 of the housing 18 is beveled so as to provide an angled distal end 22 having a top portion 32 and bottom portion 34. The distal end 22 of the housing is formed so as to allow the bottom portion 34 of the distal end 22 to extend beyond the top portion 32 and beyond the distal tip 6 of the endoscope 8 when it is inserted into the sheath 12 (FIGS. 3 and 4). The distal end can be beveled to achieve this or other configurations can be used. The second opening 26 extends through the bottom portion 34 of the distal end 22 of the housing 18 so that fluid flowing out of the second opening 26 will clean the distal tip 6 of the endoscope 8. The first opening 24 is unobstructed at the housing distal end 22 in order to allow the distal tip 6 of the endoscope 8 to project past the top portion 32 of distal end 22. If beveled, the angle of the bevel can conform to the shape of the distal end of an endoscope, and can be generally about 30° or 45°. As illustrated in FIG. 5, in another embodiment of the housing 18, the distal end 22 can be scoop-shaped in order to extend over the distal tip 6 of a 70° endoscope. Preferredly, the bevel angles of the distal end 22 can accommodate a 0°, 30°, 70° or 120° endoscope.

When the disposable sheath 12 is used as part of an endoscopic cleaning/stream irrigation system 10, a source of fluid 13 is connected to a reversible pump 14 that includes a fluid control mechanism 16. In a preferred embodiment, the disposable sheath 12 is constructed so as to be used with Smith and Nephew Inc.'s HydraClear Endoscopic Cleaning System.

Figure 7:
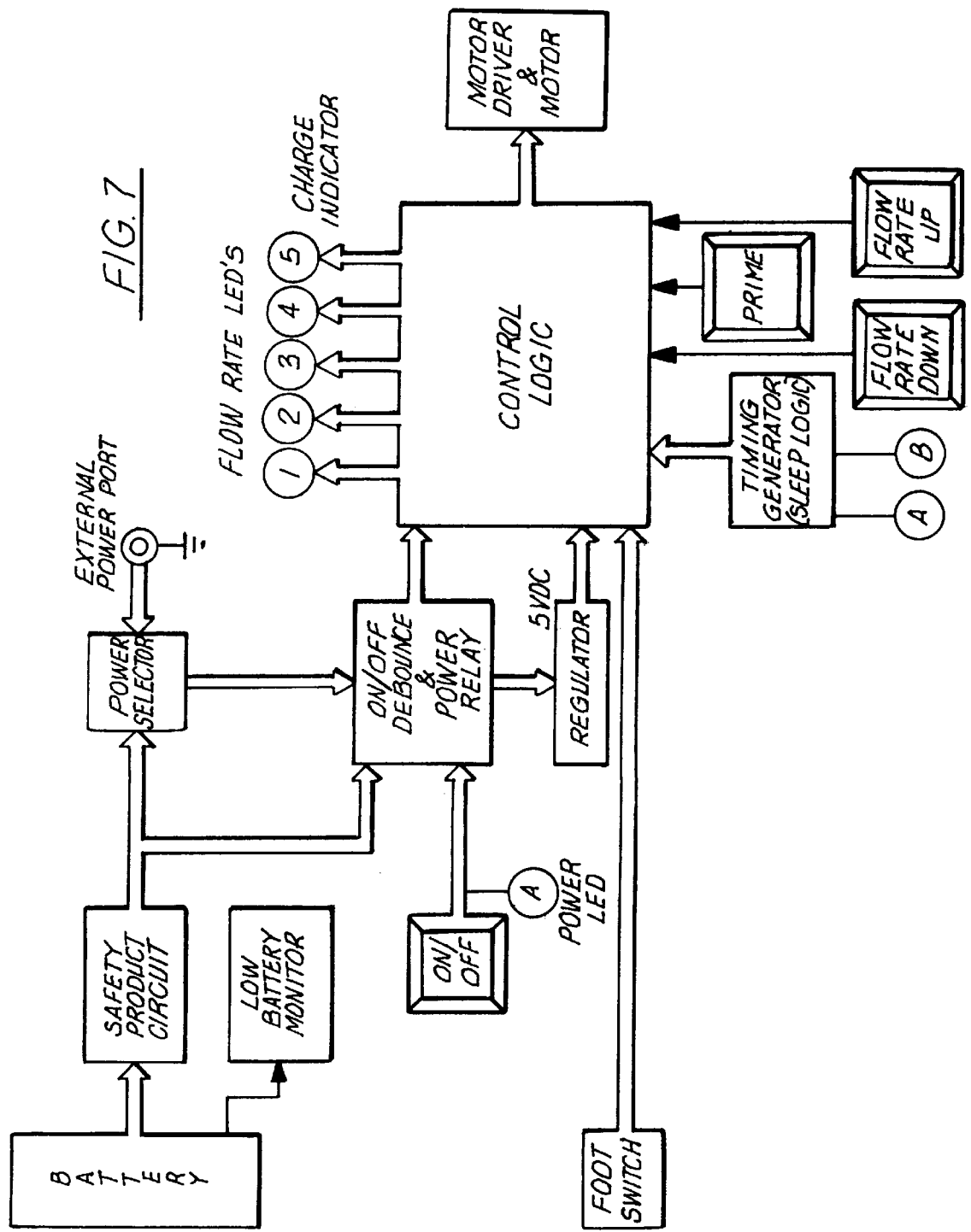
FIG. 7 is a functional flow diagram of the pump of the system of FIG. 6.

The fluid control mechanism 16 preferably is a two pedal foot control mechanism connected to the pump 14 in order to allow the surgeon to control the direction of fluid flow through the second opening 26 and nipple 30. A first foot pedal 36 is used for the "cleaning" mode and a second foot petal 38 is used for the "irrigation" mode. The first pedal 36 is changeable from first or off position to a second or on position when the pedal 36 is depressed. The first pedal 36 is automatically spring-biased toward the first position when the pedal 36 is not depressed. When the first pedal 36 is depressed for the clean mode, the pump 14 is signaled to supply fluid to the conduit 31 at a predetermined rate and also, if desired, to project a fluid stream into the surgical view. When the first pedal 36 is allowed to move to its first or off position, the pump 14 automatically reverses the flow of fluid for a relatively short period of time at a predetermined rate to evacuate fluid from the distal end 6 of the endoscope 8. When the first pedal 36 is depressed once again, pump 14 supplies a predetermined amount of fluid for a relatively short period of time to the conduit. Thus, to clean the distal end 6 of the endoscope 8, the user presses the first pedal 36. Once the distal end 6 of the endoscope 8 is clean, the user removes his/her foot from the pedal 36. This stops the pump 14 and it automatically reverses preferably 0.63 ml of fluid at a rate of 100 ml/min. This helps remove any fluid left on the lens of the endoscope 8. When the user is ready to clean the scope again, he/she presses the first pedal 36 and the pump 14 briefly goes into a "fill" mode. This mode is to compensate for the strong automatic reversal mode. When the pump 14 completes the reverse, the saline or fluid in the line reverses several inches away from the distal end 6 of the endoscope 8 and sheath 12. To get the saline back into the sheath 12 quickly, the "fill" mode of the pump 14 operates at a rate of 100 ml/min with a fluid amount of approximately 0.55 ml before switching automatically to clean. FIG. 7 illustrates the functional flow diagram of the pump 14.

The second foot pedal 38 is used for the irrigation mode and enables the surgeon to irrigate blood, tissue or other bodily material from the surgical site quickly with the touch of the second pedal 38. To initiate the irrigation mode, the user presses the second foot pedal 38. The pump 14 preferably has five preset fluid positions to choose from: 10 ml/min., 20 ml/min., 30 ml/min., 40 ml/min. and 50 ml/min of fluid flow per minute. Once the surgical area is irrigated, the user removes his/her foot from the pedal 38. This stops the pump 14 and the automatic reverse described above happens. Thus, the reversible pump 14 supplies fluid to the conduit 31 at a predetermined rate in response to a signal triggered by the surgeon, and automatically reverses the flow of fluid for a relatively short period of time at a predetermined rate to evacuate fluid from the distal end 6 of the endoscope 8 when the first signal is stopped.

The inventive disposable sheath 12 is used for cleaning and stream irrigating the viewing end of a medical endoscope of the type that includes an elongated bundle of optical fibers for viewing an internal surgical site. The viewing end of the endoscope includes a distal tip 6 adapted to transmit images from the surgical site through the fibers. The disposable sheath 12 is used by first mounting the sheath 12 on the endoscope 8 in a locked position so that the endoscope 8 extends through the first opening 24 in the housing 18. Tubing for supplying fluid 13 to the second opening 26 of the housing 18 is attached to the nipple 30 with the other end of the tubing being attached to the reversible pump 14. The pump 14 includes preferably two foot pedals 34, 36 for operating the reversible pump 14. By manipulation of the foot pedals 34, 36, fluid is supplied to the sheath 12 through the second opening 26 at a predetermined rate in response to a signal triggered by the surgeon. The pump 14 and foot pedals 34, 36 allow for automatically reversing the flow of fluid for a relatively short period of time at a predetermined rate to evacuate fluid from the distal end 6 of the endoscope 8 when either foot pedal 34, 36 is released. When one of the foot pedals 34, 36 is again depressed, a predetermined amount of fluid is supplied to the second housing 26 for a relatively short period of time when the signal is once again triggered. When one of the foot pedals 34, 36 is once again depressed in a second position, fluid is again supplied to the conduit 31 at a predetermined rate.

Preferably, the pump is a rotary peristaltic pump which will automatically reverse direction when the foot switch is released. In the dual pedal configuration, preferably the right foot switch is for the clean mode and the left foot switch is for the irrigate mode.

Although particular embodiments of the invention have been described in detail for purposes of illustration, various modifications made be made without departing from the spirit and scope of the invention. Accordingly, the invention is not to be limited except by the appended claims. Those skilled in the art will recognize changes which may be made in form and structure, which do not depart from the spirit of the invention already described in this specification and embodied in the claims which follow.

We claim:

1. An improved disposable sheath for use in combination with a endoscope of the type that includes an elongated bundle of optical fibers for viewing an internal surgical site, the endoscope including a distal tip adapted to transmit images from the surgical site through the fibers, the improved sheath comprising:

a. an elongated housing with proximal and distal ends;
   b. a first opening extending through the housing for receiving an endoscope;
   c. a second opening extending though the housing configured for an inflow and outflow of fluid through the housing;
   d. the proximal end of the housing being adapted to secure the housing relative to an endoscope and connect the second opening to a source of fluid;
   e. the distal end having top and bottom portions;
   f. the first opening being unobstructed at the distal end of the housing to allow an endoscope's distal tip to project past the top potion of the housing distal end;
   g. the bottom portion of the housing distal end extending beyond an endoscope's distal tip;
   h. the second opening extending through the bottom portion of the housing distal end so that fluid flowing out of the second opening will clean an endoscope's distal tip, project a fluid stream into the surgical view and provide for the inflow of fluid from a surgical site.

2. The improved sheath of claim 1, wherein the housing is formed of single piece of a sterilizable polymer.

3. The improved sheath of claim 1, wherein the first and second openings extend parallel to each through the housing.

4. The improved sheath of claim 1, wherein the first opening is generally round in cross section and the second opening is generally arc-shaped.

5. The improved sheath of claim 1, wherein the distal end of the housing is beveled so the top and bottom portions define opposed ends of the bevel.

6. The improved sheath of claim 5, wherein the distal end of the housing is beveled at about 45 degrees.

7. The improved sheath of claim 5, wherein the distal end of the housing is beveled at about 30 degrees.

8. The improved sheath of claim 1, wherein the bottom portion of the distal end of the housing is scoop shaped and extends over an endoscope's distal tip.

9. The improved sheath of claim 1, wherein the top portion includes a beveled end extending toward the bottom portion.

10. The improved sheath of claim 1, further including a lock on the proximal end for locking the housing to an endoscope.

11. The improved sheath of claim 10, and further including a hand grip on the proximal end of the housing.

12. The improved sheath of claim 1, wherein the reversible pump is connected to a mechanism that allows for the selective directional controlling of the fluid flow through the second opening.

* * * * *